United States Patent [19]

Reiffenrath et al.

[11] Patent Number: 5,209,868
[45] Date of Patent: May 11, 1993

[54] TRIFLUOROMETHYLCYCLOHEXANE DERIVATIVES

[75] Inventors: Volker Reiffenrath, Rossdorf; Eike Poetsch, Mühltal; Hans-Adolf Kurmeier, Seeheim-Jugenheim; Georg Weber, Erzhausen; Reinhard Hittich, Modautal; Hans-Michael Kompter, Weiterstadt; Herbert Plach, Darmstadt, all of Fed. Rep. of Germany

[73] Assignee: Merck Patent Gesellschaft mit beschrankter Haftung, Darmstadt, Fed. Rep. of Germany

[21] Appl. No.: 499,414

[22] PCT Filed: Mar. 31, 1990

[86] PCT No.: PCT/EP90/00513

§ 371 Date: Jun. 15, 1990

§ 102(e) Date: Jun. 15, 1990

[87] PCT Pub. No.: WO90/12073

PCT Pub. Date: Oct. 18, 1990

[30] Foreign Application Priority Data

Apr. 8, 1989 [DE] Fed. Rep. of Germany ....... 3911621
Sep. 9, 1989 [DE] Fed. Rep. of Germany ....... 3930119

[51] Int. Cl.$^5$ .................. C09K 19/30; C09K 19/52; C07D 319/06; C07C 19/08
[52] U.S. Cl. .................. 252/299.63; 252/299.61; 252/299.01; 252/299.62; 252/299.66; 252/299.68; 544/298; 549/369; 570/129; 546/339
[58] Field of Search .............. 252/299.63, 299.61, 252/299.01; 549/369; 544/298; 570/129

[56] References Cited

U.S. PATENT DOCUMENTS

| | | | |
|---|---|---|---|
| 4,348,298 | 9/1982 | Zaschke et al. | 252/299.1 |
| 4,398,803 | 8/1983 | Pohl et al. | 252/299.63 X |
| 4,402,849 | 9/1983 | Krause et al. | 252/299.61 |
| 4,505,837 | 3/1985 | Romer et al. | 252/299.6 |
| 4,684,476 | 8/1987 | Kitano et al. | 252/299.61 |
| 4,871,469 | 10/1989 | Reiffenrath et al. | 252/299.61 |

FOREIGN PATENT DOCUMENTS 3828543 3/1990 Fed. Rep. of Germany .
2162515 2/1986 United Kingdom .

OTHER PUBLICATIONS

Finkenzeller et al., "Physical Properties of Liquid Crystals: III. Dielectric Permittivities," E. Merck, Darmstadt, Germany.

Primary Examiner—Robert L. Stoll
Assistant Examiner—C. Harris
Attorney, Agent, or Firm—Millen, White, Zelano & Branigan

[57] ABSTRACT

Disclosed are trifluoromethylcyclohexane derivatives of the formula I

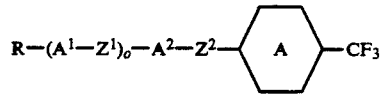

wherein

R is an alkyl or alkenyl radical having up to 18 C atoms which is unsubstituted or substituted by CN or by at least one halogen, and in which one or more non-adjacent $CH_2$ groups may be replaced by a radical selected from the group comprising —O—, —S—, —CO—, —O—CO—, —CO—O— and —C≡C—, $A^1$ and $A^2$ are each, independently of one another,
 a) a 1,4-phenylene radical, in which one or two CH groups may be replaced by N,
 b) a 1,4-cyclohexylene radical, in which one or two non-adjacent $CH_2$ groups may be replaced by —O— or —S—,
 c) a 1,4-cyclohexenylene, piperidine-1,4-diyl, 1,4-bicyclo[2,2,2]-octylene or naphthalene-2,6-diyl radical, it being possible for the radicals a) and b) to be mono-substituted or polysubstituted by halogen atoms or cyano and/or methyl groups, (Abstract continued on next page.)

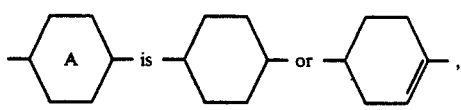
$Z^1$ and $Z^2$ are each, independently of one another, —CO—O—, —O—CH—, —CH$_2$CH$_2$—, —CH(CN)—CH$_2$—, —CH$_2$—CH(CN)—, —CH=CH—, —OCH$_2$—, —CH$_2$O—, —CH=N—, —N=CH—, —NO=N—, —N=NO—, —N=N— or a single bond, and
o is 0, 1 or 2.
These compounds can be used as components of liquid-crystalline media for electrooptical display elements, in particular for matrix liquid-crystal displays.
10 Claims, No Drawings

TRIFLUOROMETHYLCYCLOHEXANE DERIVATIVES

The invention relates to trifluoromethylcyclohexane derivatives of the formula I

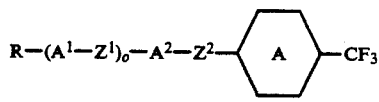
  I where

R is an alkyl or alkenyl radical having up to 18 C atoms which is unsubstituted or substituted by CN or by at least one halogen, and in which one or more non-adjacent CHz groups may be replaced by a radical selected from the group comprising —O—, —S—, —CO—, —O—CO—, —CO—O— and —C≡C—, $A^1$ and $A^2$ are each, independently of one another,
a) a 1,4-phenylene radical, in which one or two CH groups may be replaced by N,
b) a 1,4-cyclohexylene radical, in which one or two non-adjacent CHz groups may be replaced by —O— or —S—,
c) a 1,4-cyclohexenylene, piperidine-1,4-diyl, 1,4-bicyclo[2,2,2]-octylene or naphthalene-2,6-diyl radical, it being possible for the radicals a) and b) to be mono-substituted or polysubstituted by halogen atoms or cyano and/or methyl groups,

$Z^1$ and $Z^2$ are each, independently of one another, —CO—O—, —O—CO—, —CH$_2$CH$_2$—, —CH(CN)—CH$_2$—, —CH$_2$—CN(CN)—, —CH=CH—, —OCH$_2$—, —CH$_2$O—, —CH=N—, —N=CH—, —NO=N—, —N=NO—, —N=N— or a single bond, and o is 0, 1 or 2.

The invention furthermore relates to the use of these compounds as components of liquid-crystalline media, and to liquid-crystal and electrooptical display elements which contain the liquid-crystalline media according to the invention.

The compounds of the formula I can be used as components of liquid-crystalline media, in particular for displays based on the principle of the twisted cell, including highly twisted variants thereof, such as, for example, STN or SBE, the guest-host effect, the effect of deformation of aligned phases or the effect of dynamic scattering in particular for matrix liquid-crystal displays (MLC displays).

The invention had the object of finding novel stable liquid-crystalline or mesogenic compounds which are suitable as components of liquid-crystalline media and in particular have comparatively low viscosity and a moderate positive dielectric anisotropy.

It has now been found that compounds of the formula I are pre-eminently suitable as components of liquid-crystalline phases. In particular, they have comparatively low viscosities. Using them, stable liquidcrystalline phases which have a broad mesophase range, advantageous values for the optical and dielectric anisotropy and are at the same time distinguished by very favourable values for the specific resistance can be obtained. This gives considerable advantages, in particular in the case of media for matrix liquid-crystal displays (MLC displays) or supertwist displays.

Similar compounds having liquid-crystalline properties have already been disclosed, for example in EP-A-0,0193,191 (sic), JP 59/078,129 or JP 58/198,427. In these, however, the trifluoromethyl group is linked to a phenyl radical and they therefore generally have comparatively disadvantageous values for the optical anisotropy and are significantly inferior to the compounds according to the invention for modern display applications.

JP 60/69,059 and JP 63/238,030 disclose similar compounds which, however, contain a

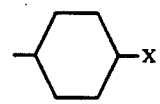

in which X is CN, F or Cl.

Furthermore, compounds are known which contain a trifluoromethylcyclohexyl group, but do not have any mesogenic properties. Thus, for example, JP 63/51,354 describes cyclohexanecarboxylic acids which are substituted by a trifluoromethyl group, and the preparation thereof.

K. W. Baldrin, M. J. T. Robinson [Tetrahedron 33, 1663–1668 (1977)] carried out studies on various 1-trifluromethyl-3-substituted cyclohexanes.

Furthermore, DE-OS 3,022,818 mentions, in a general formula, 4,4'-disubstituted bicyclohexylenes, inter alia, as mixture components of liquid-crystalline media, it also being possible for one of the substituents to be a trifluoromethyl group.

However, there is no explicit mention therein of a compound of this type nor of the preparation thereof, neither is it possible for a person skilled in the art to deduce the excellent properties of these compounds nor a preparation procedure.

In addition, the provision of the compounds of the formula I very generally considerably extends the range of liquid-crystalline substances which are suitable, from various applicational points of view, for the preparation of liquid-crystalline mixtures.

The compounds of the formula I have a broad field of application. Depending on the choice of substituents, these compounds can be used as base materials from which liquid-crystalline phases are predominantly composed; however, compounds of the formula I can also be added to liquid-crystalline base materials from other classes of compound, in order, for example, to influence the dielectric and/or optical anisotropy of a dielectric of this type and/or to optimize its threshold voltage and/or its viscosity and/or its specific resistance.

In the pure state, the compounds of the formula I are colorless and form liquid-crystalline mesophases in a favorable,temperature range for electrooptical use. They are stable chemically, thermally and to light.

The invention thus relates to the compounds of the formula I, in particular the compounds of the formula I in which the radicals $A^1$ and $A^2$ are each, independently of one another, a cyclohexylene radical, in which one or two non-adjacent $CH_2$ groups may be replaced by —O— or —S—.

The invention furthermore relates to the use of these compounds as components of liquid-crystalline media. The invention furthermore relates to liquid-crystalline media containing at least one compound of the formula I, and to liquid-crystal display elements, in particular electrooptical display elements, in particular matrix liquid-crystal displays, which contain media of this type.

For reasons of simplicity, X below is -$CF_3$, Cyc is a 1,4-cyclohexylene or a 1,4-cyclohexenylene radical, Dio is a 1,3-dioxane-2,5-diyl radical, Dit is a 1,3-dithiane-2,5-diyl radical, Phe is a 1,4-phenylene radical, Pyd is a pyridine-2,5-diyl radical, Pyr is a pyrimidine-2,5-diyl radical and Bi is a bicyclo(2,2,2)octylene radical, where Cyc and/or Phe may be unsubstituted or monosubstituted or disubstituted by F or CN.

Accordingly, the compounds of the formula I include compounds, having two rings, of the sub-formulae Ia to Ic (sic):

| | |
|---|---|
| R—$A^2$—Cyc—X | Ia |
| A—$A^2$—$Z^2$—Cyc—X | Ib |

Compounds having three rings, of the sub-formulae Ic to If:

| | |
|---|---|
| R—$A^1$—$A^2$—Cyc—X | Ic |
| R—$A^1$—$Z^1$—$A^2$—Cyc—X | Id |
| R—$A^1$—$A^2$—$Z^2$—Cyc—X | Ie |
| R—$A^1$—$Z^1$—$A^2$—$Z^2$—Cyc—X | If | and compounds, having four rings, of the sub-formulae Ig to Ih (sic):

| | |
|---|---|
| R—$A^1$—$A^1$—$A^2$—Cyc—X | Ig |
| R—$A^1$—$Z^1$—$A^1$—$A^2$—Cyc—X | Ih |
| R—$A^1$—$A^1$—$Z^1$—$A^2$—Cyc—X | Ii |
| R—$A^1$—$A^1$—$A^2$—$Z^2$—Cyc—X | Ij |
| R—$A^1$—$Z^1$—$A^1$—$Z^1$—$A^2$—Cyc—X | Ik |
| R—$A^1$—$Z^1$—$A^1$—$A^2$—$Z^2$—Cyc—X | Il |
| R—$A^1$—$A^1$—$Z^1$—$A^2$—$Z^2$—Cyc—X | Im |
| R—$A^1$—$Z^1$—$A^1$—$Z^1$—$A^2$—$Z^2$—Cyc—X | In |

Of these, those of the sub-formulae Ia, Ib, Ic, Id, Ie, If, Ig, Ih, Ii and Il are particularly preferred.

Preferred compounds of the formula I are the 4-trifluoromethylbicyclohexyl derivatives of the formula I1,

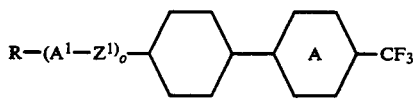

I1 in which R, $A^1$, $Z^1$ —A— and o are as defined above, in particular those in which o is 0 or 1.

Preferred compounds of the formula I are furthermore 2-(4-trifluoromethylcyclohexyl)dioxane derivatives of the formula I2

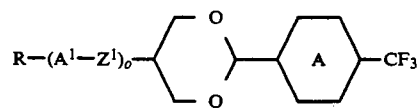

I2 in which R, $A^1$, $Z^1$, —A— and o are as defined above, in particular those of the formula I2 in which o is 0 and R is a group of the formula $(CH_2)_n$—X, where n is 1 to 10, and X is F, Cl $CH=CH_2$, $CH=CH—C_mH_{2m+1}$, $C\equiv CH$ or H, in which m is 1 to 10.

The preferred compounds of the sub-formula Ia include those of the sub-formulae Iaa to Iae:

| | |
|---|---|
| R—Phe—Cyc—X | Iaa |
| R—Cyc—Cyc—X | Iab |
| R—Dio—Cyc—X | Iac |
| R—Pyr—Cyc—X | Iad |
| R—Pyd—Cyc—X | Iae |

Of these, those of the formulae Iaa and Iab are particularly preferred.

The preferred compounds of the sub-formula Ib include those of the sub-formulae Iba to Ibl:

| | |
|---|---|
| R—Phe—$CH_2CH_2$—Cyc—X | Iba |
| R—Cyc—$CH_2CH_2$—Cyc—X | Ibb |
| R—Cyc—$CH_2O$—Cyc—X | Ibc |
| R—Phe—$CH_2O$—Cyc—X | Ibd |
| R—Phe—CO—O—Cyc—X | Ibe |
| R—Cyc—CO—O—Cyc—X | Ibf |
| R—Cyc—C≡C—Cyc—X | Ibg |
| R—Phe—C≡C—Cyc—X | Ibh |
| R—Phe—$OCH_2$—Cyc—X | Ibi |
| R—Cyc—$OCH_2$—Cyc—X | Ibj |
| R—Cyc—O—CO—Cyc—X | Ibk |
| R—Phe—O—CO—Cyc—X | Ibl |

The preferred compounds of the sub-formula Ic include those of the sub-formulae Ica to Ich:

| | |
|---|---|
| R—Cyc—Cyc—Cyc—X | Ica |
| R—Phe—Cyc—Cyc—X | Icb |
| R—Phe—Phe—Cyc—X | Icc |
| R—Cyc—Phe—Cyc—X | Icd |
| R—Pyd—Phe—Cyc—X | Ice |
| R—Pyd—Cyc—Cyc—X | Icf |
| R—Pyr—Cyc—Cyc—X | Icg |

-continued

R—Pyr—Phe—Cyc—X   Ich

Of these, those of the formulae Ica, Icb and Icc are particularly preferred.

The preferred compounds of the sub-formula Id include those of the sub-formulae Ida to Idi:

R—Phe—$Z^1$—Phe—Cyc—X   Ida
R—Phe—$Z^1$—Cyc—Cyc—X   Idb
R—Cyc—$Z^1$—Cyc—Cyc—X   Idc
R—Pyr—$Z^1$—Cyc—Cyc—X   Idd
R—Pyd—$Z^1$—Cyc—Cyc—X   Ide
R—Pyd—$Z^1$—Phe—Cyc—X   Idf
R—Pyr—$Z^1$—Phe—Cyc—X   Idg
R—Cyc—$Z^1$—Dio—Cyc—X   Idh
R—Phe—$Z^1$—Dio—Cyc—X   Idi

The preferred compounds of the sub-formula Ie include those of the sub-formulae Iea to Iei:

R—Phe—Phe—$Z^2$—Cyc—X   Iea
R—Phe—Cyc—$Z^2$—Cyc—X   Ieb
R—Cyc—Cyc—$Z^2$—Cyc—X   Iec
R—Cyc—Phe—$Z^2$—Cyc—X   Ied
R—Pyr—Phe—$Z^2$—Cyc—X   Iee
R—Pyd—Phe—$Z^2$—Cyc—X   Ief
R—Phe—Pyr—$Z^2$—Cyc—X   Ieg
R—Phe—Pyd—$Z^2$—Cyc—X   Ieh
R—Phe—Dio—$Z^2$—Cyc—X   Iei

The preferred compounds of the sub-formula If include those of the sub-formulae Ifa to Ifg R—Phe—$Z^1$—Phe—$Z^2$—Cyc—X   Ifa
R—Phe—$Z^1$—Cyc—$Z^2$—Cyc—X   Ifb
R—Cyc—$Z^1$—Cyc—$Z^2$—Cyc—X   Ifc
R—Cyc—$Z^1$—Phe—$Z^2$—Cyc—X   Ifd
R—Cyc—$Z^1$—Bi—$Z^2$—Cyc—X   Ife
R—Cyc—$Z^1$—Dio—$Z^2$—Cyc—X   Iff
R—Dio—$Z^1$—Cyc—$Z^2$—Cyc—X   Ifg In the compounds of the formulae above and below, Cyc-X is preferably a 4-trifluoromethylcyclohexyl group, in particular a trans-4-trifluoromethylcyclohexyl group.

In the compounds of the sub-formulae Ib, Id, Ie, If and Ih to In which contain one or more $Z^1$ and/or $Z^2$ bridges, these bridging members are preferably —CO—O—, —O—CO—, —CH$_2$CH$_2$—, CH$_2$O—, —OCH$_2$— or —C≡C—, in particular —CH$_2$CH$_2$—, —CO—O— or O—CO—.

R is preferably alkyl, furthermore alkoxy, F, Cl or CN. $A^1$ and/or $A^2$ are preferably Phe, Cyc, Che, Pyr or Dio. The compounds of the formula I preferably contain not more than one of the radicals Bi, Pyd, Pyr, Dio or Dit.

Preferred compounds of the formula I and of all the sub-formulae are those in which $A^1$, $A^2$, $A^3$ and/or $A^4$ are 1,4-phenylene which is monosubstituted or disubstituted by F or monosubstituted by CN. These are, in particular, 2-fluoro-1,4-phenylene, 3-fluoro-1,4-phenylene and 2,3-difluoro-1,4-phenylene, and 2-cyano-1,4-phenylene and 3-cyano-1,4-phenylene.

$Z^1$ and $Z^2$ are preferably a single bond, —CO—O—, —O—CO—and —CH$_2$CH$_2$—, and secondarily preferably —CH$_2$O— and —OCH$_2$—.

If R is halogen, it is preferably F, Cl, Br and furthermore I.

If R is an alkyl radical and/or an alkoxy radical, it may be straight-chain or branched. It is preferably straight-chain, has 2, 3, 4, 5, 6 or 7 C atoms and is accordingly preferably ethyl, propyl, butyl, pentyl, hexyl, heptyl, ethoxy, propoxy, butoxy, pentoxy, hexoxy or heptoxy, furthermore methyl, octyl, nonyl, decyl, undecyl, dodecyl, tridecyl, tetradecyl, pentadecyl, methoxy, octoxy, nonoxy, decoxy, undecoxy, dodecoxy, tridecoxy or tetradecoxy.

Oxaalkyl is preferably straight-chain 2-oxapropyl (=methoxymethyl), 2- (=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, or 2-, 3-, 4-, 5-, 6-, 7-, 8- or 9-oxadecyl.

If R is an alkenyl radical, it may be straightchain or branched. It is preferably straight-chain and has 2 to 10 C atoms. It is accordingly particularly vinyl, prop-1- or -2-enyl, but-1-, -2- or -3-enyl, pent-1-, -2-, -3- or -4-enyl, hex-1-, -2-, -3-, -4- or -5-enyl, hept-1-, -2-, -3-, -4-, -5- or -6-enyl, oct-1-, -2-, -3-, -4-, -5-, -6- or -7-enyl, non-1-, -2-, -3-, -4-, -5-, -6-, -7- or -8-enyl, or dec-1-, -2-, -3-, -4-, -5-, -6-, -7-, -8- or -9-enyl.

If R is an alkyl radical in which one CH$_2$ group has been replaced by —O— and one has been replaced by —CO—, these are preferably adjacent. These thus contain an acyloxy group —CO—O— or an oxycarbonyl group —O—CO—. These are preferably straight-chain and have 2 to 6 C atoms. They are accordingly particularly acetyloxy, propionyloxy, butyryloxy, pentanoyloxy, hexanoyloxy, acetyloxymethyl, propionyloxymethyl, butyryloxymethyl, pentanoyloxymethyl, 2-acetyloxyethyl, 2-propionyloxyethyl, 2-butyryloxyethyl, 3-acetyloxypropyl, 3-propionyloxypropyl, 4-acetyloxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxacarbonyl)ethyl (sic), 2-(propoxycarbonyl)ethyl, 1,3-(methoxycarbonyl)propyl,3-(ethoxycarbonyl)propyl and 4-(methoxycarbonyl)butyl.

If R is an alkenyl radical in which one CH$_2$ group has been replaced by CO or CO—O or O—CO, it may be straight-chain or branched. It is preferably straightchain and has 4 to 13 C atoms. It is accordingly particularly acryloyloxymethyl, 2-acryloyloxyethyl, 3-acryloyloxypropyl, 4-acryloyloxybutyl, 5-acryloyloxypentyl, 6-acryloyloxyhexyl, 7-acryloyloxyheptyl, 8-acryloyloxyoctyl, 9-acryloyloxynonyl, 10-acryloyloxydecyl, methacryloyloxymethyl, 2-methacryloyloxyethyl, 3-methacryloyloxypropyl, 4-methacryloyloxybutyl, 5- methacryloyloxypentyl, 6-methacryloyloxyhexyl, 7-methacryloyloxyheptyl, 8-methacryloyloxyoctyl or 9-methacryloyloxynonyl.

Compounds of the formula I which contain wing groups R which are suitable for polymerization reactions are suitable for the preparation of liquid-crystalline polymers.

Compounds of the formula I containing branched wing groups R may occasionally be of importance due to better solubility in the customary liquid-crystalline base materials, but in particular as chiral dopes if they are optically active. Smectic compounds of this type are suitable as components of ferroelectric materials.

Compounds of the formula I having $S_A$ phases are suitable, for example, for thermally addressed displays.

Branched groups of this type generally contain not more than one chain branch. Preferred branched radicals R are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy, 1-methylheptoxy, 2-oxa-3-methylbutyl, 3-oxa-4-methylpentyl, 4-methylhexyl, 2-nonyl, 2-decyl, 2-dodecyl, 6-methyloctoxy, 6-methyloctaroyloxy,5-methylheptyloxycarbonyl,2-methylbutyryloxy, 3-methylvaleryloxy, 4-methylhexanoyloxy, 2-chloro-4-methylvaleryloxy, 2-chloro-3-methylvaleryloxy, 2-methyl-3-oxapentyl and 2-methyl-3-oxahexyl.

If R is an alkyl radical in which two or more $CH_2$ groups have been replaced by —O— and/or —CO—O—, it may be straight-chain or branched It is preferably branched and has 3 to 12 C atoms. It is accordingly particularly biscarboxymeth-yl, 2,2-biscarboxyethyl, 3,3-biscarboxypropyl, 4,4-biscarboxybutyl, 5,5-biscarboxypentyl, 6,6-biscarboxyhexyl, 7,7-biscarboxyheptyl, 8,8-biscarboxyoctyl,9,9-biscarboxynonyl10,10-biscarboxydecyl, bis(methoxycarbonyl)-methyl, 2,2-bis(methoxycarbonyl)ethyl, 3,3-bis(methoxycarbonyl)propyl, 4,4-bis(methoxycarbonyl)butyl, 5,5-bis(methoxycarbonyl)pentyl, 6,6-bis(methoxycarbonyl)hexyl, 7,7-bis(methoxycarbonyl)heptyl, 8,8-bis(-methoxycarbonyl)octyl, bis(ethoxycarbonyl)methyl, 2,2-bis(ethoxycarbonyl)ethyl, 3,3-bis(ethoxycarbonyl)-propyl, 4,4-bis(ethoxycarbonyl)butyl or 5,5-bis(ethoxycarbonyl)hexyl.

Compounds of the formula I which contain wing groups R which are suitable for polycondensations are suitable for the preparation of liquid-crystalline polycondensates.

The formula I covers the racemates of these compounds and the optical antipodes, and mixtures thereof.

Of these compounds of the formula I and the subformulae, those are preferred in which at least one of the radicals present therein has one of the preferred meanings indicated.

In the compounds of the formula I, those stereoisomers in which the rings Cyc and piperidine are trans1,4-disubstituted are preferred. Those of the abovementioned formulae which contain one or more groups Pyd, Pyr and/or Dio in each case include the two 2,5-positional isomers.

The 1,4-cyclohexenylene group preferably has the following structures:

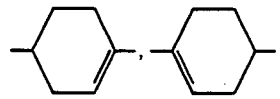

The compounds of the formula I are prepared by methods known per se, as described in the literature (for example in the standard works, such as Houben-Weyl, Methoden der Organischen Chemie [Methods of Organic Chemistry], Georg-Thieme-Verlag, Stuttgart, Vol. IX, pp. 867 ff.), to be precise under reaction conditions which are known and suitable for the reactions mentioned. Use can also be made here of variants which are known per se, but are not described in greater detail here.

The trifluoromethylcyclohexyl compounds of the formula I according to the invention can be prepared, for example, by reacting the cyclohexanecarboxylic acids conforming to the formula I with dialkylaminosulfur trifluorides, for example DAST (diethylaminosulfur trifluoride) [W. J. Middleton, J. Org. Chem. 40, 574, (1975)] or sulfur tetrafluoride [A. Haus, M. Spitzer, M. Lieb, Chem. Ber. 121 (1988), 1329], in accordance with the equation

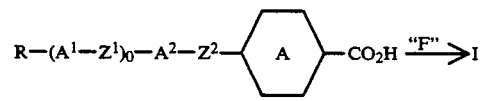

It is furthermore possible to prepare the compounds of the formula I from the corresponding trifluorophenyl compounds by catalytic hydrogenation [for example analogous to K. W. Baldrin, M. J. T. Robinson, Tetrahedron 33, 1663–1668 (1977)]

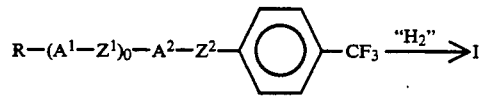

In addition, the compounds of the formula I can be prepared by reacting the corresponding 4-substituted 1-trifluoromethylcyclohexanes of the formula II T,0132

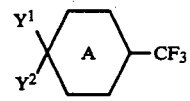

in which
$Y^1$ is -$(CH_2)_n$—$Y^3$, —CHO or CN,
$Y^2$ is H,
or
$Y^1$ and $Y^2$ together are O
$Y^3$ is OH, halogen or O—$SO_2$—$C_7H_7$, and
n is 0, 1 or 2,
with the appropriately substituted compounds of the formula III R—$(A^1$—$Z^1)_0$—$A^2$—$Z^3$III.

The novel compounds of the formula II likewise form the subject-matter of the invention.

The compounds of the formula I in which $Z^2$ is $CH_2O$ or $OCH_2$ are obtained, for example, by etherification of the compounds of the formula II in which $Y^1$ is $(CH_2)_n$—$Y^3$ using the compounds of the formula III in which $Z^3$ is $CH_2OH$ or OH.

The compounds of the formula I in which $Z^2$ is $CH_2CH_2$ can be prepared, for example, by reacting the compounds of the formula III in which $Z^3$ is $CH_2$Met and Met is Li, Na, K, ⁺P($C_6H_5$)$_3$ (sic) or P(O)(O$C_2H_5$)$_2$, with the compounds of the formula II in which $Y^1$ is CN or CHO, and by subsequent reduction of the resultant ketone or ethylene derivative.

The compounds of the formula I in which $Z^2$ is a single bond can be obtained, for example, by reacting the compounds of the formula III in which $Z^3$ is Met with the compounds of the formula II in which $Y^1$ and $Y^2$ together are O, subsequently dehydrating the product, and, if necessary, subjecting the resulting cyclohexene derivative to catalytic hydrogenation.

Furthermore, the compounds of the formula I can (lacuna) by reacting the cyclohexanones conforming to the formula I with trifluoromethyl-Met, in which Met is Li, Na, K, MgBr or MgCl or with trimethyl(trifluoromethyl)silane in the presence of a Lewis acid, such as, for example, titanium tetrachloride or zinc bromide, or in the presence of a fluoride, such as, for example, tetrabutylammonium fluoride or caesium fluoride, for example by the method of C. F. Olah et al., J.Am.Chem.Soc. 111, 393-395 (1989) and dehydrating the corresponding trifluoromethylhydrin in the presence of a dehydrating reagent.

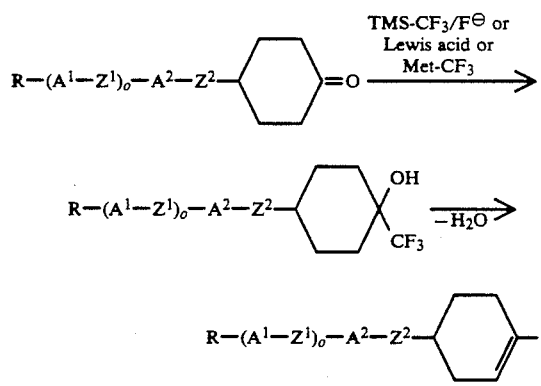

Suitable dehydrating agents are, for example, $P_2O_5$, POCl$_3$, PCl$_3$, PCl$_5$, COCl$_2$ and DAST.

In addition, the compounds of the formula I in which

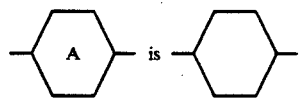

can be prepared a by (sic) DielsAlder condensation, catalyzed by a Lewis acid, of 2-trifluoromethylbutadiene with the appropriate vinyl compounds (for example by the method of T. Kojuma, T. Inuhai, J.Org.Chem. 35 (5), 1342-1348 (1970)) in accordance with scheme II.

Scheme II

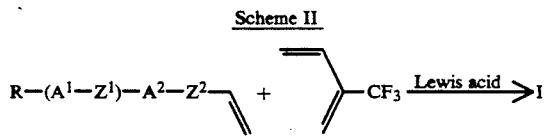

This process is preferably used to prepare the compounds of the formula I in which $Z^2$ is —O—CO, in particular also the intermediates of the formula IIa,

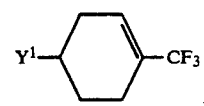

in which
$Y^1$ is CHO, CN or COOR*, and
R* is H or alkyl having 1 to 6 C atoms.

2-Trifluorobutadiene can be obtained from 1,1,1-trifluoroacetone by the method of T. Inuhai, M. Kasai, J.Org.Chem. 30 3567 (1965).

The 2-(4-trifluoromethylcyclohexyl)dioxanes of the formula I2 are prepared in accordance with Scheme III by condensation of appropriately substituted propanediols with 4-formyltrifluoromethylcyclohexane.

Scheme III

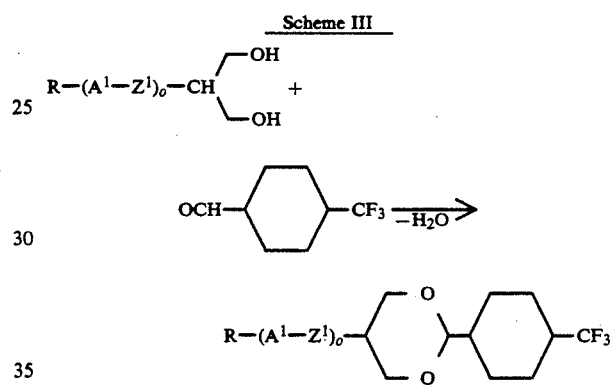

The appropriately substituted propanediols are prepared in accordance with Scheme IV by alkylation of malonic esters or analogously to the process described in DE 3,227,916:

Scheme IV:

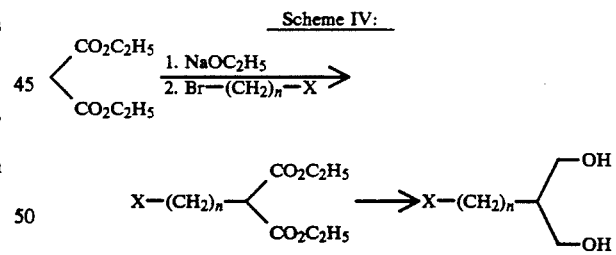

If desired, the starting materials can also be formed in situ by not isolating them from the reaction mixture, but instead immediately reacting them further to form the compounds of the formula I. Thus, the compounds of the formula I can be prepared by reducing a compound which contains one or more reducible groups and/or C—C bonds in place of H atoms, but otherwise corresponds to the formula I.

Suitable reducible groups are preferably carbonyl groups, in particular keto groups, furthermore, for example, free or esterified hydroxyl groups or aromatically bound halogen atoms. Preferred starting materials for the reduction correspond to the formula I, but can contain a cyclohexene ring, cyclohexanone ring or phenyl ring in place of a cyclohexane ring and/or can contain a —CH=CH— group in place of a —CH$_2$C-

H₂— group and/or can contain a —CO— group in place of a —CH₂— group and/or can contain a free or functionally (for example in the form of its p-toluenesulfonate) derived OH group in place o+an H atom.

The reduction can be carried out, for example, by catalytic hydrogenation at temperatures between about 0° and about 200° and at pressures between about 1 and 200 bar in an inert solvent, for example an alcohol, such as methanol, ethanol or isopropanol, an ether, such as tetrahydrofuran (THF) or dioxane, an ester, such as ethyl acetate, a carboxylic acid, such as acetic acid, or a hydrocarbon, such as cyclohexane. Suitable catalysts are preferably noble metals, such as Pt or Pd, which can be employed in the form of oxides (for example $PtO_2$ or PdO), on a support (for example Pd on charcoal, calcium carbonate or strontium carbonate) or in finely divided form.

Ketones can also be reduced by the methods of Clemmensen (using zinc, zinc amalgam or tin and hydrochloric acid, preferably in aqueous-alcoholic solution or in the heterogeneous phase with water/toluene at temperatures between about 80° and 120°) or Wolff-Kishner (using hydrazine, preferably in the presence of alkali, such as KOH or NaOH, in a high-boiling solvent, such as diethylene glycol or triethylene glycol, at temperatures between about 100° and 200°) to form the corresponding compounds of the formula I which contain alkyl groups and/or —CH₂CH₂— bridges.

In addition, reductions using complex hydrides are possible. For example, arylsulfonyloxy groups can be removed reductively using LiAlH₄, in particular p-toluenesulfonyloxymethyl groups are reduced to methyl groups, preferably in an inert solvent, such as diethyl ether or THF, at temperatures of between about 0° and 100°. Double bonds can be hydrogenated using NaBH₄ or tributyltin hydride in methanol.

Compounds of the formula I which contain 1,4-cyclohexenylene radicals in place of 1,4-phenylene radicals but otherwise correspond to the formula I can be oxidized, for example, using DDQ (dichlorodicyanobenzoquinone) in a suitable solvent.

Esters of the formula I can also be obtained by esterification of appropriate carboxylic acids (or reactive derivatives thereof) using alcohols or phenols (or reactive derivatives thereof) or by the DCC method (DCC=dicyclohexylcarbodiimide).

The corresponding carboxylic acids and alcohols or phenols are known or can be prepared analogously to known processes.

Suitable reactive derivatives of the carboxylic acids mentioned are, in particular, the acyl halides, above all the chlorides and bromides, furthermore the anhydrides, for example also mixed anhydrides, azides or esters, in particular alkyl esters having 1-4 C atoms in the alkyl group.

Suitable reactive derivatives of the alcohols or phenols mentioned are, in particular, the corresponding metal alkoholates or phenolates, preferably of an alkali metal such as sodium or potassium.

The esterification is advantageously carried out in the presence of an inert solvent. Highly suitable solvents are, in particular, ethers, such as diethyl ether, di-n-butyl ether, THF, dioxane or anisole, ketones, such as acetone, butanone or cyclohexanone, amides, such as DMF or hexamethylphosphoric triamide, hydrocarbons, such as benzene, toluene or xylene, halogenated hydrocarbons, such as tetrachloromethane, dichloromethane or tetrachloroethylene, and sulfoxides, such as dimethyl sulfoxide or sulfolane.

In order to prepare nitriles of the formula I, appropriate acid amides, for example those in which a CONH₂ group replaces the CN radical, can be dehydrated. The amides can be obtained, for example, from appropriate esters or acyl halides by reaction with ammonia. Suitable water-eliminating agents are, for example, inorganic acid chlorides, such as $SOCl_2$, $PCl_3$, $PCl_5$, $POCl_3$, $SO_2Cl_2$, $COCl_2$, furthermore $P_2O_5$, $P_2S_5$, $AlCl_3$ (for example as a double compound with NaCl), aromatic sulfonic acids and sulfonyl halides. The reaction can be carried out in the presence or absence of an inert solvent at temperatures between about 0° and 150°; suitable solvents are, for example, bases, such as pyridine or triethylamine, aromatic hydrocarbons, such as benzene, toluene or xylene, or amides, such as DMF.

To prepare the abovementioned nitriles of the formula I, it is also possible to react appropriate acyl halides, preferably the chlorides, with sulfamide, preferably in an inert solvent, such as tetramethylene sulfone, at temperatures between about 80° and 150°, preferably at 120°. After customary work-up, the nitriles can be isolated directly.

Ethers of the formula I can be obtained by etherification of corresponding hydroxyl compounds, preferably corresponding phenols, the hydroxyl compound expediently first being converted into a corresponding metal derivative, for example into the corresponding alkali metal alcoholate or alkali metal phenolate by treatment with NaH, NaNH₂, NaOH, KOH, Na₂CO₃ or K₂CO₃. This can then be reacted with the appropriate alkyl halide, sulfonate or dialkyl sulfate, expediently in an inert solvent, such as acetone, 1,2-dimethoxyethane, DMF or dimethyl sulfoxide, or also in an excess of aqueous or aqueous-alcoholic NaOH or KOH, at temperatures between about 20° and 100°.

To prepare nitriles of the formula I, it is also possible to react appropriate chlorine, bromine or iodine compounds of the formula I with a cyanide, preferably with a metal cyanide, such as NaCN, KCN or Cu₂(CN)₂, for example in the presence of pyridine in an inert solvent, such as DMF or N-methylpyrrolidone, at temperatures between 20° and 200°.

Compounds of the formula I in which $A^1$ is substituted by at least one F atom and/or one CN group can also be obtained from the corresponding diazonium salts by replacement of the diazonium group by a fluorine atom or by a CN group, for example by the methods of Schiemann or Sandmeyer.

Dioxane derivatives and dithiane derivatives of the formula I are expediently prepared by reacting an appropriate aldehyde (or a reactive derivative thereof) with an appropriate 1,3-diol (or a reactive derivative thereof) or an appropriate 1,3-dithiol, preferably in the presence of an inert solvent, such as benzene or toluene, and/or in the presence of a catalyst, for example a strong acid such as sulfuric acid, benzenesulfonic acid or p-toluenesulfonic acid, at temperatures between about 20° and about 150°, preferably between 80° and 120°. Suitable reactive derivatives of the starting materials are primarily acetals.

Some of the aldehydes, 1,3-diols and 1,3-dithiols mentioned, and some of the reactive derivatives thereof, are known, and some be prepared without difficulties from compounds known from the literature by standard methods of organic chemistry. For example, the aldehydes can be obtained by oxidation of corresponding alcohols or by reduction of nitriles or corresponding carboxylic acids or derivatives thereof, the diols can be obtained by reduction of corresponding diesters, and the dithiols can be obtained by reaction of corresponding dihalides with NaSH.

The liquid-crystalline media according to the invention preferably contain 2 to 40, in particular 4 to 30, components as further constituents besides one or more compounds according to the invention. These media very particularly preferably contain 7 to 25 components besides one or more compounds according to the invention. These further constituents are preferably selected from nematic or nematogenic (monotropic or isotropic) substances, in particular substances from the classes of the azoxybenzenes, benzylideneanilines, biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid and of cyclohexylcyclohexanecarboxylic acid, phenylcyclohexanes, cyclohexylbiphenyls, phenylcyclohexylcyclohexanes, cyclohexylcyclohexanes, cyclohexylcyclohexenes, cyclohexylcyclohexylcyclohexenes, 1,4-bis-cyclohexylbenzenes, 4,4'-bis-cyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)ethanes, 1-cyclohexyl-2-biphenylylethanes, 1-phenyl-2-cyclohexylphenylethanes, optionally halogenated stilbenes, benzyl phenyl ethers, tolans and substituted cinnamic acids. The 1,4-phenylene groups in these compounds may also be fluorinated.

The most important compounds suitable as further constituents of media according to the invention can be characterized by the formulae 1, 2, 3, 4 and 5:

$$R'-L-E-R'' \quad 1$$
$$R'-L-COO-E-R'' \quad 2$$
$$R'-L-OOC-E-R'' \quad 3$$
$$R'-L-CH_2CH_2-E-R'' \quad 4$$
$$R'-L-C\equiv C-E-R'' \quad 5$$

In the formulae 1, 2, 3, 4 and 5, L and E, which may be identical or different, are in each case, independently of one another, a divalent radical from the group formed by —Phe—, —Cyc—, —Phe—Phe, —Phe—Cyc—, —Cyc—Cyc—, —Pyr—, —Dio—, —G—Phe— and —G—Cyc—and their mirror images, where Phe is unsubstituted or fluorine-substituted 1,4-phenylene, Cyc is trans-1,4-cyclohexylene or 1,4-cyclohexenylene, Pyr is pyrimidine-2,5-diyl or pyridine-2,5-diyl, Dio is 1,3-dioxane-2,5-diyl and G is 2-(trans-1,4-cyclohexyl)ethyl, pyrimidine-2,5-diyl, pyridine-2,5-diyl or 1,3-dioxane-2,5-diyl.

One of the radicals L and E is preferably Cyc, Phe or Pyr. E is preferably Cyc, Phe or Phe-Cyc. The media according to the invention preferably contain one or more components selected from the compounds of the formulae 1, 2, 3, 4 and 5 in which L and E are selected from the group comprising Cyc, Phe and Pyr and simultaneously one or more components selected from the compounds of the formulae 1, 2, 3, 4 and 5 in which one of the radicals L and E is selected from the group comprising Cyc, Phe and Pyr and the other radical is selected from the group comprising —Phe—Phe—, —Phe—Cyc—, —Cyc—Cyc—, —G—Phe— and —G—Cyc—, and optionally one or more components selected from the compounds of the formulae 1, 2, 3, 4 and 5 in which the radicals L and E are selected from the group comprising —Phe—Cyc—, —Cyc—Cyc—, —G—Phe— and —G—Cyc—.

In the compounds of the sub-formulae 1a, 2a, 3a, 4a and 5a, R' and R" are in each case, independently of one another, alkyl, alkenyl, alkoxy, alkenyloxy or alkanoyloxy having up to 8 carbon atoms. In most of these compounds, R' and R" are different from one another, one of these radicals usually being alkyl or alkenyl In the compounds of the sub-formulae 1b, 2b, 3b, 4b and 5b, R" is —CN, —CF$_3$, F, Cl or —NCS; in this case, R has the meaning given for the compounds of the sub-formulae 1a to 5a and is preferably alkyl or alkenyl. However, other variants of the proposed substituents in the compounds of the formulae 1, 2, 3, 4 and 5 are common. Many such substances or alternatively mixtures thereof are commercially available. All these substances can be obtained by methods which are known from the literature or analogously thereto.

Besides components from the group comprising the compounds 1a, 2a, 3a, 4a and 5a (Group 1), the media according to the invention also preferably contain components from the group comprising the compounds 1b, 2b, 3b, 4b and 5b (Group 2), whose proportions are preferably as follows:

Group 1: 20 to 90%, in particular 30 to 90%,
Group 2: 10 to 80%, in particular 10 to 50%, the sum of the proportions of the compounds according to the invention and of the compounds from Groups 1 and 2 adding up to 100%.

The media according to the invention preferably contain 1 to 40%, in particular preferably 5 to 30%, of compounds according to the invention. Further preferred media are those which contain more than 40%, in particular 45 to 90%, of compounds according to the invention. The media preferably contain three, four or five compounds according to the invention.

The media according to the invention are prepared in a manner which is customary per se. In general, the components are dissolved in one another, expediently at elevated temperature. By means of suitable additives, the liquid-crystalline phases can be modified in accordance with the invention in a manner such that they can be used in all types of liquid-crystal display elements which have hitherto been disclosed. Additives of this type are known to those skilled in the art and are described in detail in the literature (H. Kelker/R. Hatz, Handbook of Liquid Crystals, Verlag Chemie, Weinheim, 1980). For example, pleochroic dyes can be added for the production of coloured guest-host systems, or substances can be added to modify the dielectric anisotropy, the viscosity and/or the orientation of the nematic phases.

The media according to the invention are particularly suitable for use in MLC displays.

The examples below are intended to illustrate the invention without representing a limitation. mp. melting point, cp.=clear point. Above and below, percentages are per cent by weight,, all temperatures are indicated in degrees Celsius. "Customary work-up" means that water is added, the mixture is extracted with methylene chloride, the organic phase is separated off, dried and evaporated, the product is purified by crystallization and/or chromatography.

In addition, the abbreviations have the following meanings:

C: crystalline-solid state, S: smectic phase (the index characterizes the phase type), N: nematic state, Ch: cholesteric phase, I: isotropic phase. The number between two symbols indicates the conversion temperature in degrees Celsius.

| DAST | Diethylaminosulfur trifluoride |
|------|-------------------------------|
| DCC | Dicyclohexylcarbodiimide |
| DDQ | Dichlorodicyanobenzoquinone |
| DIBALH | Diisobutylaluminium hydride |
| DMSO | Dimethyl sulfoxide |
| POT | Potassium tertiary-butanolate |
| THF | Tetrahydrofuran |
| pTSOH | p-Toluenesulfonic acid |

EXAMPLE 1 trans-4-Trifluoromethylcyclohexanecarboxylic acid

A mixture of 0.47 mol of ethyl 4-trifluoromethylbenzoate (prepared from 4-trifluoromethylbenzoyl chloride, ethanol and pyridine), 1000 ml of ethanol and 20 g of rhodium/activated charcoal (5%) is hydrogenated for 5 hours under a pressure of 5 bar and at a temperature of 60° C. The ethyl 4-trifluoromethylcyclohexanecarboxylate (cis/trans =87%/13%) obtained after removal of the catalyst by filtration and removal of the solvent is, without prior purification, suspended in 300 ml of water and treated with 70 g of 30% sodium hydroxide solution, and the mixture is briefly heated to boiling and stirred at room temperature for 18 hours. Acidification using hydrochloric acid gives the carboxylic acid as a cis/trans mixture.

A mixture of 0.38 mol of this acid and 150 ml of thionyl chloride is boiled for 48 hours. After the excess thionyl chloride has been removed by distillation, 500 ml of water and 100 ml of a 30% sodium hydroxide solution are added, and the reaction mixture is stirred at 60° C. for 2 hours. Acidification and recrystallization from petroleum ether give the pure trans/carboxylic acid having a melting point of 155° C.

EXAMPLE 2 trans-4-Trifluoromethylcyclohexanol

A mixture of 0.3 mol of 4-trifluoromethylphenol, 1000 ml of ethanol and 20 g of rhodium/activated charcoal (5%) is hydrogenated for 2 hours at a pressure of 5 bar and a temperature of 60° C. Removal of the solid components by filtration and removal of the solvent by distillation give the cyclohexanol as a cis/trans mixture (30%/70%). From this, the pure trans-compound is obtained by heating with aluminium triisopropylate in toluene in the presence of 3,3-dimethyl-2-butanone and subsequent recrystallization.

EXAMPLE 3 trans-4-Trifluoromethyl-1-formylcyclohexane 0.05 mol of trans-4-trifluoromethylcyclohexanecarboxylic acid (prepared as in Example 1) is added dropwise to 100 ml of a solution of isobutylmagnesium bromide in ether (1 mol/1) and 0.3 mmol of dichlorobis[π-cyclopentadienyl]titanium at 0° C., and the mixture is stirred at room temperature for 4 hours. 30 ml of a 4 normal hydrochloric acid are added, and customary workup gives the product as a colourless oil.

EXAMPLE 4 trans,trans-4'-propylbicylohexyl trans-4-trifluoromethylcyclohexanecarboxylate

A mixture of 0.005 mol of trans-4-trifluoromethylcyclohexanecarboxylic acid, 0.005 mol of trans,trans-4-propylbicylcohexyl-4'-ol, 100 ml of dichloromethane, 0.005 mol of 4-N,N-dimethylaminopyridine and 0.007 mol of DCC is stirred at room temperature for 2 hours. The solid components are removed by filtration, and customary work-up gives the product as a colourless solid, C 89 S$_B$ 165 I, Δn 0.065, Δε+10.01.

The following are prepared analogously

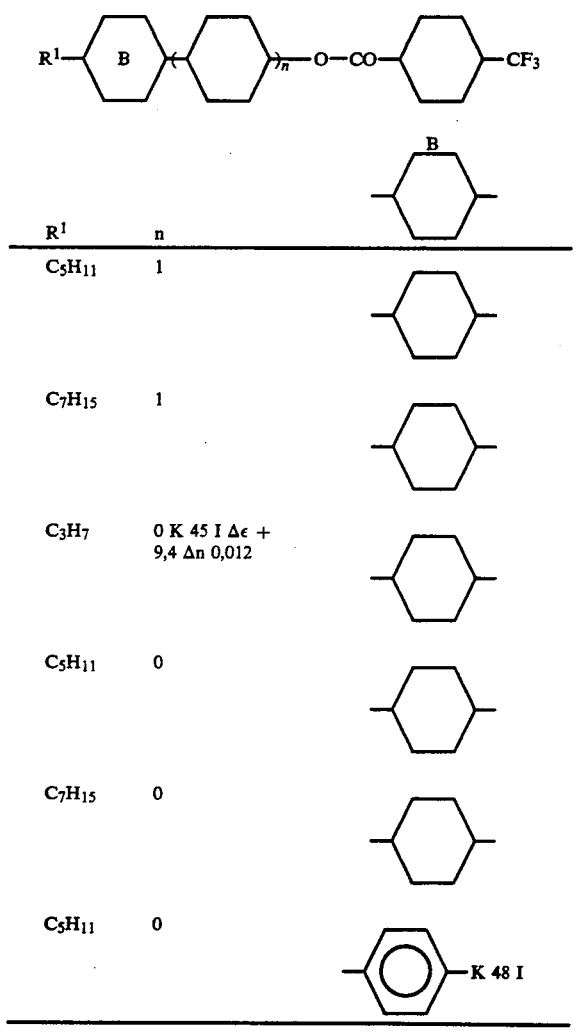

EXAMPLE 5 trans-4-trifluoromethylcyclohexyl trans-4-pentylcyclohexanecarboxylate 0.005 mol of trans-4-pentylcyclohexanecarboxylic acid are esterified analogously to Example 4 using 0.005 mol of trans-4-trifluoromethylcyclohexanol (prepared as in Example 2). The product is obtained as a colourless solid.

The following are prepared analogously:

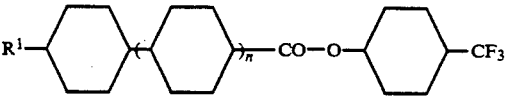

| R¹ | n |
|---|---|
| C₃H₇ | 0 |
| C₇H₁₅ | 0 |
| C₃H₇ | 1 |
| C₅H₁₁ | 1 |
| C₇H₁₅ | 1 |

EXAMPLE 6 trans-4-Heptylcyclohexylmethyl trans-4-trifluoromethylcyclohexyl ether

A mixture of 0.11 mol of trans-4-heptylcyclohexylmethyl bromide and 80 ml of THF is added at 0° C. to a mixture of 0.1 mol of sodium (trans-4-trifluoromethylcyclohexanolate) (prepared from 0.1 mol of trans-4-trifluoromethylcyclohexanol and 0.1 mol of sodium hydride) and 200 ml of THF. The mixture is stirred at 60° C. for 3 hours, and customary work-up gives the product as a colourless solid.

The following are prepared analogously:

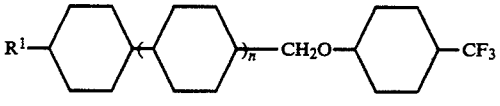

| R¹ | n |
|---|---|
| C₃H₇ | 0 |
| C₅H₁₁ | 0 |
| C₃H₇ | 1 |
| C₅H₁₁ | 1 |
| C₇H₁₅ | 1 |

Using trans-4-trifluoromethylcyclohexylmethyl bromide (prepared from trans-4-trifluorocyclohexanecarboxylic acid by reduction using lithium aluminium hydride and subsequent bromination using phosphorus tribromide) and trans-4-alkylcyclohexanols, the following are prepared analogously:

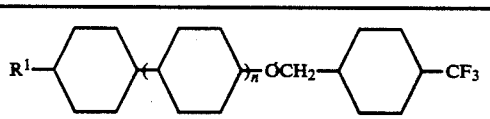

| R¹ | n |
|---|---|
| C₃H₇ | 0 |
| C₅H₁₁ | 0 |
| C₇H₁₅ | 0 |
| C₃H₇ | 1 |
| C₅H₁₁ | 1 |
| C₇H₁₅ | 1 |

EXAMPLE 7

1-(trans-4-Propylcyclohexyl)-2-(trans-4-trifluoromethylcyclohexyl)ethene

A mixture of 0.2 mol of (trans-4-propylcyclohexylmethyl)triphenylphosphonium bromide (prepared from trans-4-propylcyclohexylmethyl bromide and triphenylphosphine) and 150 ml of DMSO gives (sic) at 0° C. to a mixture of 0.2 mol of sodium hydride and 100 ml of DMSO. After the mixture has been stirred at room temperature for 10 minutes, a mixture of 0.2 mol of trans-4-trifluoromethyl-1-formyulcyclohexane (prepared as in Example 3) and 50 ml of DMSO is added dropwise. The mixture is warmed for 1 hour at 65° C. and subjected to customary work-up. The product is obtained as a colourless dye (sic).

The following are prepared analogously:

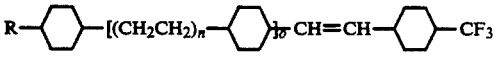

| R | o | n |
|---|---|---|
| C₂H₅ | 0 | 0 |
| C₅H₁₁ | 0 | 0 |
| C₇H₁₅ | 0 | 0 |
| C₃H₇ | 1 | 0 |
| C₅H₁₁ | 1 | 0 |
| C₇H₁₅ | 1 | 0 |
| C₃H₇ | 1 | 1 |
| C₅H₁₁ | 1 | 1 |
| C₇H₁₅ | 1 | 1 |

EXAMPLE 8

1-(trans-4-Propylcyclohexyl)-2-(trans-4-trifluoromethylcyclohexyl)ethane

A mixture of 0.1 mol of 1-(trans-4-propylcyclohexyl)-2-(trans-4-trifluoromethylcyclohexyl)ethene, 200 ml of methanol and 5 g of palladium/activated charcoal (15%) is hydrogenated for 2 hours under a pressure of 2 bar and at a temperature of 50° C. Customary work-up gives the product as a colourless solid.

The following are prepared analogously:

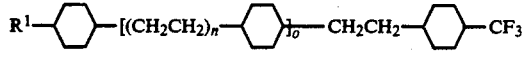

| R¹ | o | n | |
|---|---|---|---|
| C₅H₁₁ | 0 | 0 | K 48 I, Δε +6.3, Δn 0.025 |
| C₇H₁₅ | 0 | 0 | |
| C₃H₇ | 1 | 0 | K 157 S_B (156) N 158,5 I, Δε +8.7, Δn 0.054 |
| C₅H₁₁ | 1 | 0 | |
| C₇H₁₅ | 1 | 0 | |
| C₃H₇ | 1 | 1 | |
| C₅H₁₁ | 1 | 1 | |
| C₇H₁₅ | 1 | 1 | |

EXAMPLE 9 trans,trans-4'-Propyl-4-trifluoromethylbicyclohexane

A mixture of 0.35 mol of trans,trans-4'-pentylbicyclohexyl-4-carboxylic acid and 0.9 mol of sulfur tetrafluoride are (sic) warmed for 10 days at 70° C. in an autoclave. The product is taken up in pentane, and the solution is washed with water, dried and evaporated. Distillation and crystallization give the product, C 43 I.

The following are prepared analogously

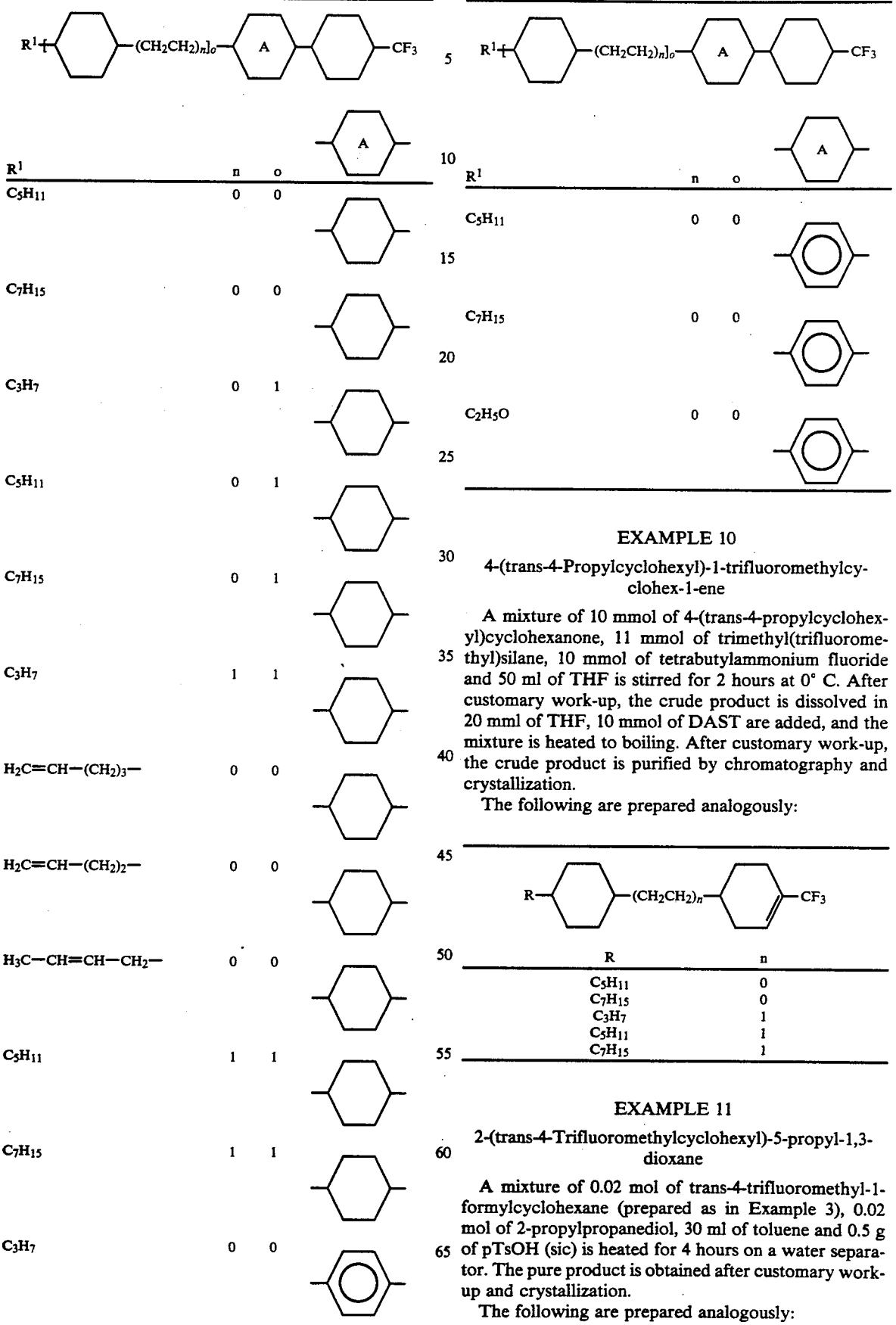

EXAMPLE 10

4-(trans-4-Propylcyclohexyl)-1-trifluoromethylcyclohex-1-ene

A mixture of 10 mmol of 4-(trans-4-propylcyclohexyl)cyclohexanone, 11 mmol of trimethyl(trifluoromethyl)silane, 10 mmol of tetrabutylammonium fluoride and 50 ml of THF is stirred for 2 hours at 0° C. After customary work-up, the crude product is dissolved in 20 mml of THF, 10 mmol of DAST are added, and the mixture is heated to boiling. After customary work-up, the crude product is purified by chromatography and crystallization.

The following are prepared analogously:

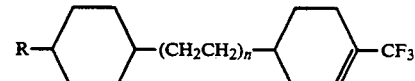

| R | n |
|---|---|
| $C_5H_{11}$ | 0 |
| $C_7H_{15}$ | 0 |
| $C_3H_7$ | 1 |
| $C_5H_{11}$ | 1 |
| $C_7H_{15}$ | 1 |

EXAMPLE 11

2-(trans-4-Trifluoromethylcyclohexyl)-5-propyl-1,3-dioxane

A mixture of 0.02 mol of trans-4-trifluoromethyl-1-formylcyclohexane (prepared as in Example 3), 0.02 mol of 2-propylpropanediol, 30 ml of toluene and 0.5 g of pTsOH (sic) is heated for 4 hours on a water separator. The pure product is obtained after customary work-up and crystallization.

The following are prepared analogously:

X—(CH$_2$)$_n$—[dioxane]—[cyclohexyl]—CF$_3$

| X | n | |
|---|---|---|
| H | 5, | K 41 S$_\beta$ 42 I |
| H | 7 | |
| H$_2$C=CH | 1 | |
| CH$_3$—CH=CH | 1 | |
| H$_2$C=CH | 2 | |
| H$_2$C=CH | 3 | |
| H$_2$C=CH | 4 | |
| H$_2$C=CH | 5 | |
| H$_2$C=CH | 6 | |
| H$_3$CO | 1 | |
| H$_3$CO | 2 | |
| H$_3$CO | 3 | |
| H$_3$CO | 4 | |
| H$_3$CO | 5 | |
| H$_3$CO | 5 | |
| X | n | |
| F | 1 | |
| F | 2 | |
| F | 3 | |
| F | 4 | |
| F | 5 | |
| F | 6 | |

EXAMPLE 12

2-(trans-4-Trifluoromethylcyclohexyl)-5-(trans-4-pentylcyclohexyl)-1,3-dioxane

A mixture of 0.02 mol of tras-4-trifluoromethyl-1-formylcyclohexane (prepared as in Example 3), 0.02 mol of 2-(trans-4-pentylcyclohexyl)propanediol (prepared as in DE 3,227,916), 30 ml of toluene and 0.5 g of pTSOH is heated for 6 hours on a water separator. The product is obtained after customary work-up and crystallization.

The following are prepared analogously:

R—[A]—(CH$_2$CH$_2$)$_n$—[dioxane]—[cyclohexyl]—CF$_3$

| R | n | A |
|---|---|---|
| C$_3$H$_7$ | 0 | cyclohexyl |
| C$_7$H$_{15}$ | 0 | cyclohexyl |
| C$_3$H$_7$ | 0 | phenyl |
| C$_5$H$_{11}$ | 0 | phenyl |
| C$_7$H$_{15}$ | 0 | phenyl |
| R | n | A |
| C$_3$H$_7$ | 1 | cyclohexyl |
| C$_5$H$_{11}$ | 1 | cyclohexyl |
| C$_7$H$_{15}$ | 1 | cyclohexyl |
| C$_5$H$_{11}$ | 1 | phenyl |

EXAMPLE 13

1-(4'-Pentyl-2'-fluorobiphenyl-4-yl)-2-(trans-4-trifluoromethylcyclohexyl)ethane Analogously to Example 7, 0.2 mol of 4'-pentyl-2'-fluorobiphenyl-4-ylmethyl bromide and 0.2 mol of trans-4-trifluoromethylformylcyclohexane (prepared as in Example 3) gives 1-(4'-pentyl-2-fluorobiphenyl-4-yl)-2-(trans-4-trifluoromethylcyclohexyl)ethene. The latter is hydrogenated analogously to Example 8 in methanol using palladium/activated charcoal (15%). Customary work-up and crystallization give the pure product.

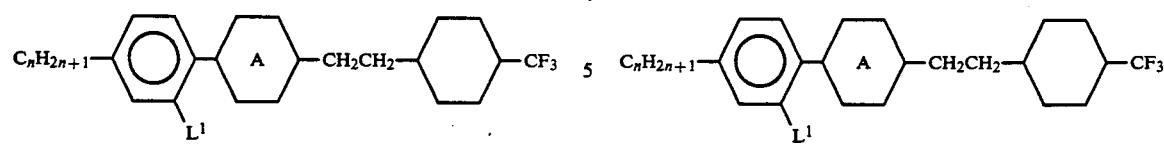

| n | L¹ | A |
|---|----|---|
| 3 | F  | phenyl |
| 7 | F  | phenyl |
| 3 | H  | phenyl |
| 5 | H  | phenyl |
| 7 | H  | phenyl |
| 3 | F  | cyclohexyl |

| n | L¹ | A |
|---|----|---|
| 5 | F  | cyclohexyl |
| 7 | F  | cyclohexyl |
| 3 | H  | cyclohexyl |
| 5 | H  | cyclohexyl |

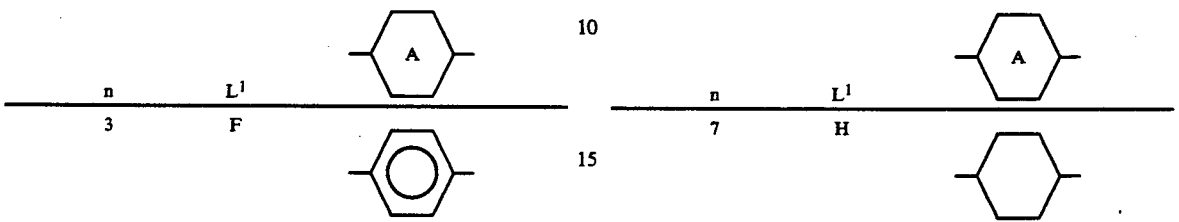

| n | L¹ | A |
|---|----|---|
| 7 | H  | cyclohexyl |

EXAMPLE 14 trans-4-(2-Ethylpyrimidin-5-yl)-trifluoromethylcyclohexane

A mixture of 0.1 mol of 2-(diethoxymethyl)butyraldehyde (attainable from diethyl 2-ethylmalonate), 0.1 mol of trans-4-trifluoromethylcyclohexylcarbamidine hydrochloride (attainable from trans-4-trifluoromethyl-1-formylcyclohexane, cf. Example 3, by treatment with hydroxylamine O-sulfonic acid in aqueous solution at 65° C. and subsequent reaction with alcoholic hydrochloric acid) and 100 ml of dimethylformamide is heated at 130° C. for 4 hours and, after a further 100 ml of dimethylformamide have been added, at 130° C. for a further 16 hours. Customary work-up gives the pure product by recrystallization.

The following are prepared analogously:

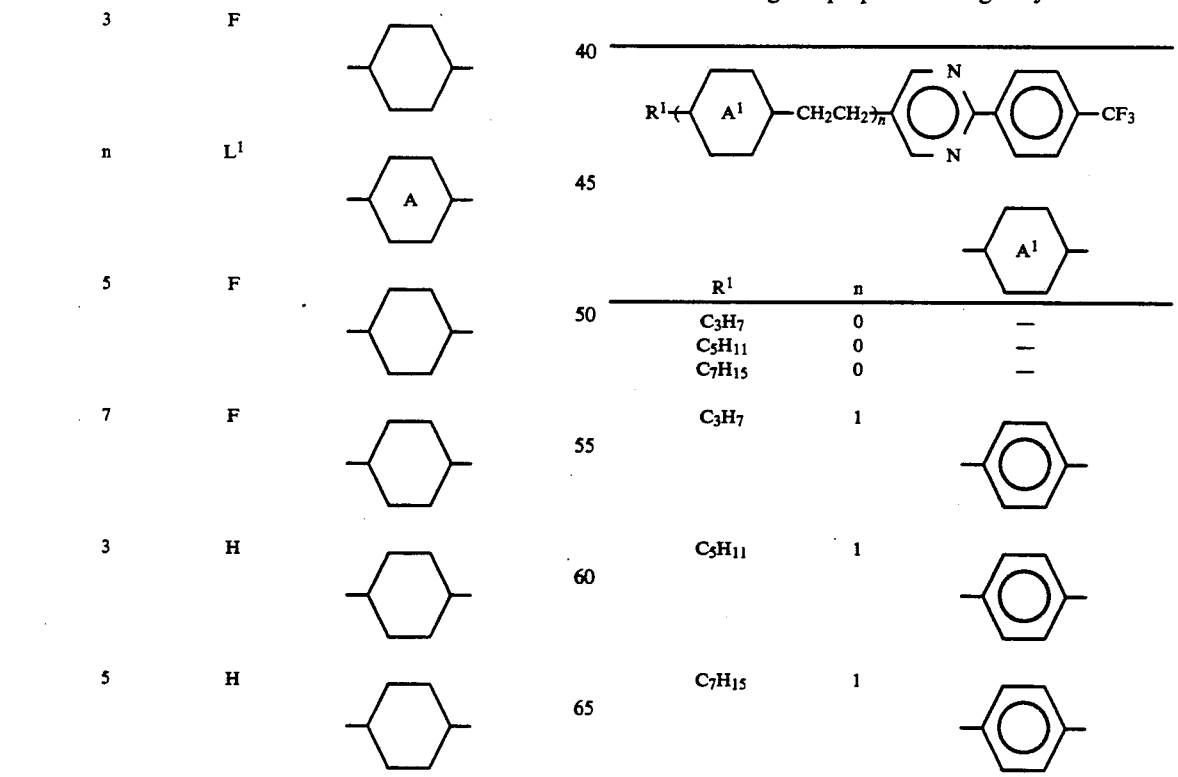

| R¹ | n | A¹ |
|----|---|----|
| C₃H₇  | 0 | — |
| C₅H₁₁ | 0 | — |
| C₇H₁₅ | 0 | — |
| C₃H₇  | 1 | phenyl |
| C₅H₁₁ | 1 | phenyl |
| C₇H₁₅ | 1 | phenyl |

-continued

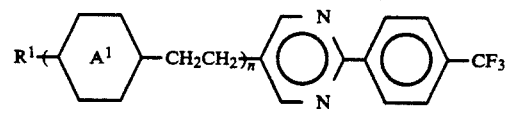

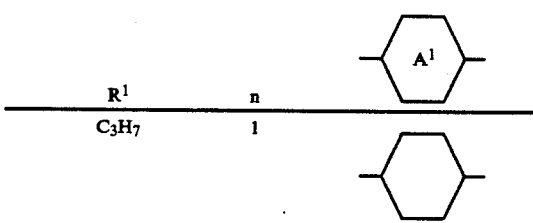

| $R^1$ | n |
|---|---|
| $C_3H_7$ | 1 |

Mixture Example A

A liquid-crystalline medium which comprises 90% by weight of a base mixture (A) comprising
24% by weight of p-(trans-propylcyclohexyl)benzonitrile
36% by weight of p-(trans-pentylcyclohexyl)benzonitrile
25% by weight of p-(trans-heptylcylcohexyl)benzonitrile (sic)
15% by weight of 4'-(trans-4-pentylcyclohexyl)-4-cyanobiphenyl and
10% of trans,trans-4-propylbicyclohexyl trans-4-trifluoromethylcyclohexanecarboxylate is prepared.

Mixture Example B

A liquid crystalline medium which comprises 90% by weight of the base mixture (A) and
10 % by weight of 2-(trans,trans-4'-propylbicyclohexyl-4-yl)-1-(trans-4-trifluoromethylcyclohexyl)ethane is prepared.

Mixture Example C

A liquid-crystalline medium which comprises 90% by weight of the base mixture (A) and
10 % by weight of 2-(trans-4-pentylcyclohexyl)-1-(trans-4-trifluoromethylcyclohexyl)ethane is prepared.

We claim:

1. A liquid-crystalline medium having at least two components, wherien one or more component is a trifluoromethylcyclohexane compound of the formula I

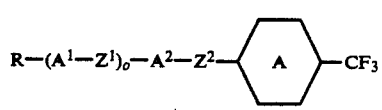

I wherein

R is an alkyl or alkenyl radical having up to 18 C atoms which is unsubstituted or substituted by CN or by at least one halogen, and in which one or more non-adjacent $CH_2$ groups may be replaced by a radical selected from the group comprising —O—, —S—, —CO—, —O—CO—, —CO—O— and —C≡C—, $A^1$ and $A^2$ are each, independently of one another,
a) a 1,4-phenylene radical, in which one or two CH groups may be replaced by N,
b) a 1,4-cyclohexylene radical, in which one or two non-adjacent $CH_2$ groups may be replaced by —O— or —S—,
c) a 1,4-cyclohexenylene, piperidine-1,4-diyl, 1,4-bicyclo[2,2,2]-octylene or naphthalene-2,6-diyl radical, it being possible for the radicals a) and b) to be monosubstituted or polysubstituted by halogen atoms or cyano and/or methyl groups,

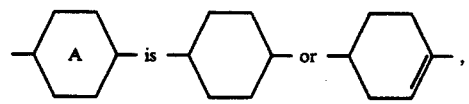

$Z^1$ and $Z^2$ are each, independently of one another, —$CH_2CH_2$—, —CH(CN)—$CH_2$—, —$CH_2$—CH(CN)—, —CH=CH—, —$OCH_2$—, —$CH_2O$—, —CH=N—, —N=CH—, —NO=N—, —N=NO—, —N=N— or a single bond, and
o is 0 or 1.

2. A liquid-crystalline medium according to claim 1, wherein
$A^1$ and $A^2$ are each, independently of one another, a 1,4-cyclohexylene radical, in which one or two non-adjacent $CH_2$ groups may be replaced by —O— or —S—.

3. A liquid-crystalline medium according to claim 1 wherein
$Z^2$ is —$CH_2CH_2$—.

4. A liquid-crystalline medium according to claim 1, containing a compound of the formula I1

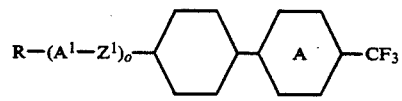

in which R, $A^1$,

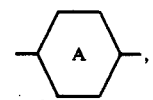

$Z^1$ and o are as defined above.

5. A liquid-crystalline medium according to claim 1, containing a 2-(trifluoromethylcyclohexyl)dioxane compound of the formula I2

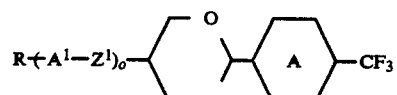

wherein R, $A^1$,

$Z^1$ and o are as defined above.

6. A liquid crystalline medium according to claim 1 containing a 2-(trifluoromethylcyclo-hexyl)dioxane compound of the formula I2a

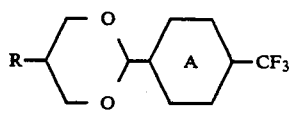

R is F—(CH2)n—, Cl—(CH2)n—, CH2=CH—(CH2)n—, CmH2m+1—CH=CH—(CH2)n—, CmH2m+1—O—(CH2)n and HC≡CH—(CH2)n and m and n are each independently 0 to 10.

7. A liquid-crystalline medium according to claim 1, containing a trifluoromethylcyclohexane compound wherein the 1,4-cyclohexylene radicals are in the trans-configuration.

8. An electrooptical electrooptical display comprising as a dielectric, a liquid-crystalline medium according to claim 1.

9. A matrix liquid-crystal display comprising as a dielectric, a liquid-crystalline medium according to claim 1.

10. A liquid-crystalline medium according to claim 1, wherein o is 0 or 1.

* * * * *